United States Patent
Du et al.

(10) Patent No.: US 10,441,293 B2
(45) Date of Patent: Oct. 15, 2019

(54) HEMOSTATIC METHOD

(71) Applicant: SOUTHERN TAIWAN UNIVERSITY OF SCIENCE AND TECHNOLOGY, Tainan (TW)

(72) Inventors: Yi-Chun Du, Tainan (TW); Bee-Yen Lim, Tainan (TW); Shi-han Chen, Tainan (TW)

(73) Assignee: Southern Taiwan University of Science and Technology, Tainan (TW)

( * ) Notice: Subject to any disclaimer, the term of this patent is extended or adjusted under 35 U.S.C. 154(b) by 294 days.

(21) Appl. No.: 15/401,388

(22) Filed: Jan. 9, 2017

(65) Prior Publication Data

US 2018/0193031 A1    Jul. 12, 2018

(51) Int. Cl.
| | |
|---|---|
| *A61B 17/132* | (2006.01) |
| *A61B 5/026* | (2006.01) |
| *A61B 5/145* | (2006.01) |
| *A61B 5/024* | (2006.01) |
| *A61B 5/02* | (2006.01) |
| *A61B 5/00* | (2006.01) |
| *A61B 17/135* | (2006.01) |
| *A61B 17/00* | (2006.01) |

(52) U.S. Cl.
CPC ......... *A61B 17/1325* (2013.01); *A61B 5/026* (2013.01); *A61B 5/024* (2013.01); *A61B 5/02042* (2013.01); *A61B 5/0261* (2013.01); *A61B 5/14542* (2013.01); *A61B 5/4836* (2013.01); *A61B 17/135* (2013.01); *A61B 2017/00022* (2013.01); *A61B 2017/00106* (2013.01); *A61B 2017/00115* (2013.01); *A61B 2017/00398* (2013.01); *A61B 2017/00716* (2013.01); *A61B 2505/05* (2013.01)

(58) Field of Classification Search
CPC ........ A61B 2017/12004; A61B 17/132; A61B 17/1325; A61B 17/135; A61B 17/1355; A61F 2013/00468
USPC .................................................. 606/201–204
See application file for complete search history.

(56) References Cited

U.S. PATENT DOCUMENTS

| | | | |
|---|---|---|---|
| 2015/0201948 A1* | 7/2015 | Kornowski | ........ A61B 5/02042 606/203 |
| 2016/0213373 A1* | 7/2016 | Drasler | .............. A61B 17/1325 |

OTHER PUBLICATIONS

Richard N. Fogoros, Systolic and Diastolic Blood Pressure, https://www.verywellhealth.com/systolic-and-diastolic-blood-pressure-1746075 (Year: 2018).*

* cited by examiner

*Primary Examiner* — Diane D Yabut
*Assistant Examiner* — Majid Jamialahmadi
(74) *Attorney, Agent, or Firm* — Rosenberg, Klein & Lee

(57) ABSTRACT

A hemostatic method is performed as follows: A) An at-puncture hemostatic pressure is applied to a puncture in a blood vessel via a main geometric side, and at least one off-puncture hemostatic pressure is applied to at least one position away from the puncture via at least one auxiliary geometric side, wherein the off-puncture hemostatic pressure acts on the blood vessel either directly or indirectly. B) During the hemostatic process, an ongoing flow velocity of the blood in the blood vessel is obtained and is reduced to lower than a normal flow velocity in the blood vessel by applying the at-puncture and off-puncture hemostatic pressures simultaneously, wherein the at-puncture and off-puncture hemostatic pressures are lower than a systolic pressure in the blood vessel.

16 Claims, 16 Drawing Sheets

A. Apply an at-puncture hemostatic pressure to a puncture in a blood vessel via a main geometric side, and apply at least one off-puncture hemostatic pressure to at least one position away from the puncture via at least one auxiliary geometric side, wherein the off-puncture hemostatic pressure acts on the blood vessel either directly or indirectly.

B. During the hemostatic process, obtain an ongoing flow velocity of the blood in the blood vessel, and render the ongoing flow velocity lower than a normal flow velocity in the blood vessel by applying the at-puncture hemostatic pressure and the off-puncture hemostatic pressure simultaneously, wherein the at-puncture hemostatic pressure and the off-puncture hemostatic pressure are lower than a systolic pressure in the blood vessel.

C. Gather information, output the information gathered, and provide a comparison result.

FIG. 1

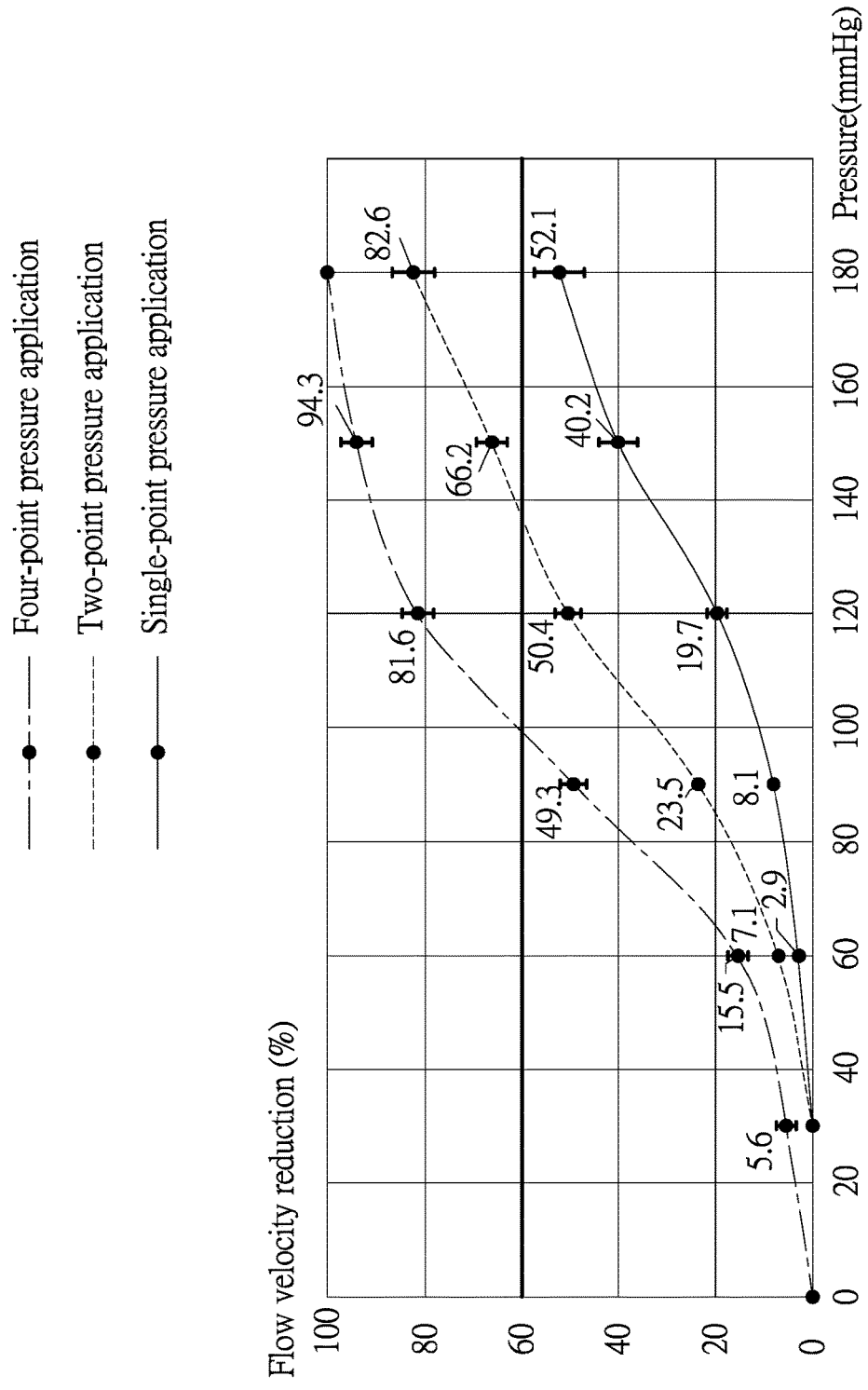
F I G. 10

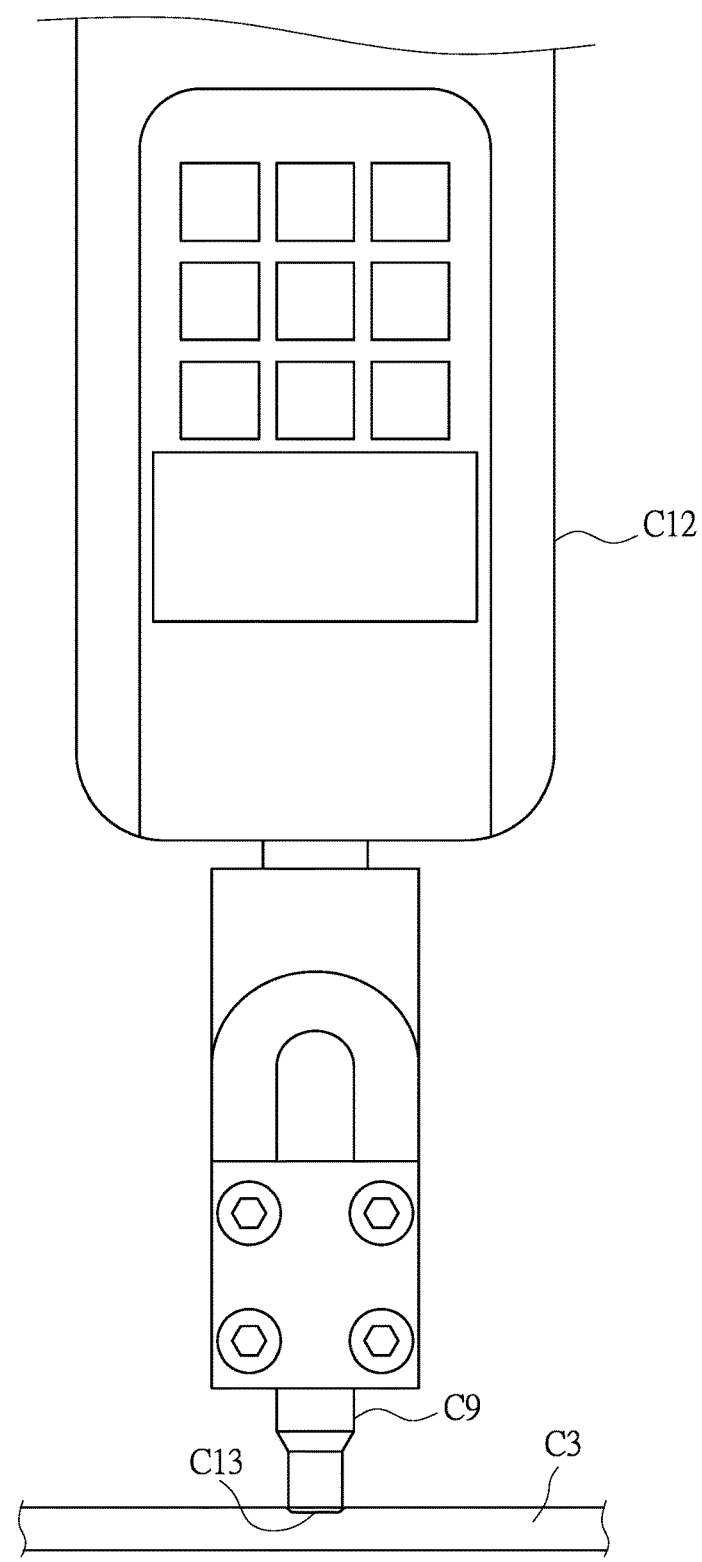
F I G . 15

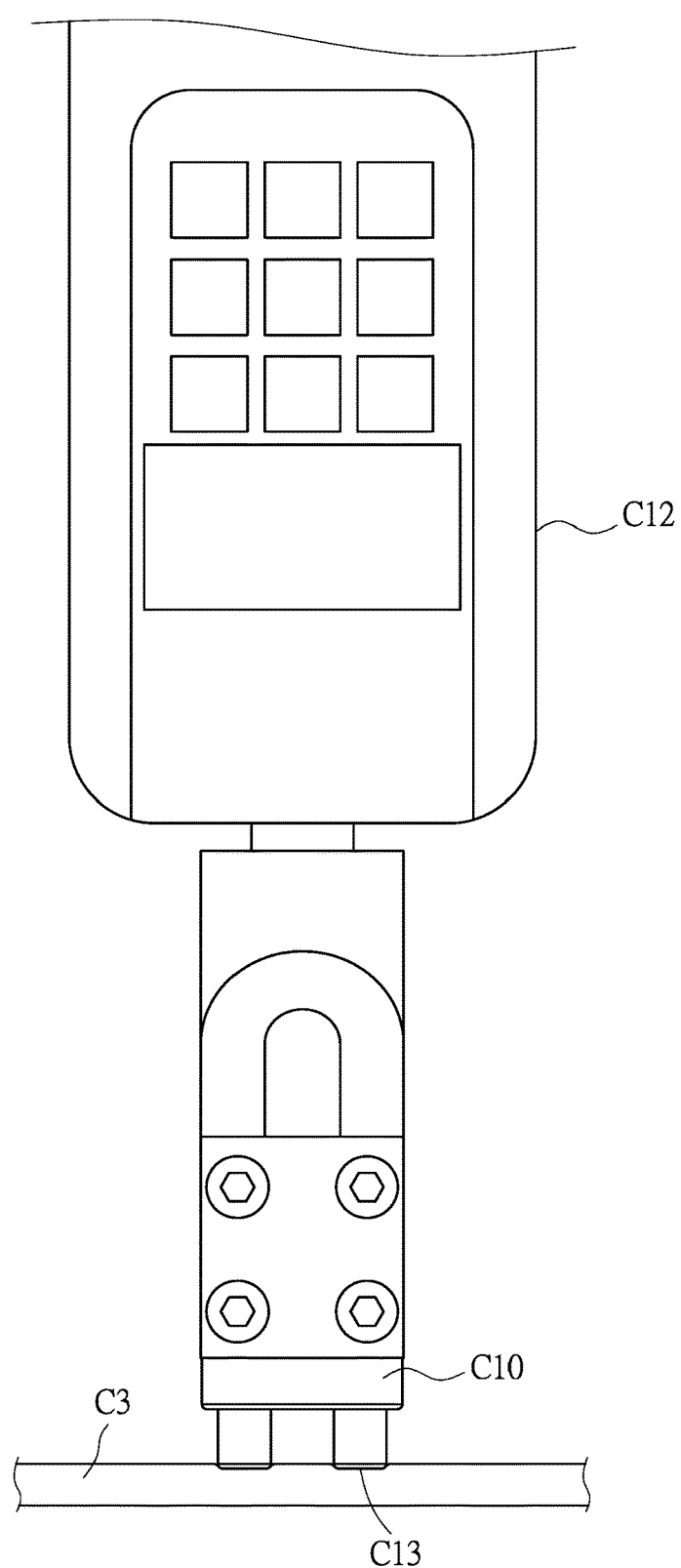
F I G . 16

HEMOSTATIC METHOD

BACKGROUND OF THE INVENTION

1. Technical Field

The present invention relates to a hemostatic method and more particularly to a method of achieving hemostasis by applying a relatively small hemostatic pressure to multiple points at the same time.

2. Description of Related Art

Clinically, a punctured or injured blood vessel needs effective hemostasis. For example, a radial artery through which percutaneous transluminal coronary angioplasty (PTCA) is performed requires hemostasis when the PTCA operation is completed, and so does a hemodialysis fistula after a dialysis session. In Taiwan, patients suffering from chronic renal failure are increasing every year. Renal failure is a condition in which a patient's kidneys have lost their functions and can no longer filter and discharge metabolic wastes from the blood such that the wastes accumulate in the body and demand regular hemodialysis in order for the patient to maintain a healthy life. Hemodialysis works in place of the patient's dysfunctional kidneys by removing excessive water, toxins, and wastes from the blood through diffusion and convection.

To receive hemodialysis, the patient must have an arteriovenous fistula (i.e., AV fistula, a fistula connected between an artery and a vein in one of the patient's arms) constructed in a surgical operation. Each time hemodialysis is performed, a nurse punctures the fistula with needles to guide the patient's blood into a dialyzer, where the blood is purified and from which the purified blood flows back to the patient's body. Such circulation of blood continues for about four to five hours until the dialysis session is completed. The needles are then removed from the fistula by the nurse. As the needles are quite thick, it is imperative that the punctures be covered with cotton and pressed with fingers immediately after the needles are withdrawn, the pressure applied and the duration of pressure application depending on the nurse's experience. Once bleeding is temporarily checked, a tourniquet is used in lieu of the pressing fingers to keep the pressure on the punctures until hemostasis is achieved.

A conventional tourniquet for clinical use is a bandage made of elastic fibers. Since the binding pressure of such a tourniquet cannot be quantified, it is very likely that too much or inadequate pressure is applied for hemostasis. If the tourniquet exerts too much pressure, the fistula may be constricted or even obstructed, thus losing its function, and tissue hypoxia may result from deficient blood supply to peripheral microcirculation. If the tourniquet fails to apply sufficient pressure, on the other hand, hemostasis simply cannot be achieved at the punctures of the hemodialysis fistula, and loss of blood ensues.

Accordingly, an improved tourniquet design as disclosed in Taiwan Utility Model Patent No. M362680, entitled "Tourniquet Device" and published on Aug. 11, 2009, emerged. This tourniquet device includes a bandage, a sensor, and a warning indicator, the latter two of which are fixed on the bandage. The bandage includes a bandage body and a hemostatic block fixed on the bandage body. The sensor is provided on the bandage and is configured for sensing the smoothness of blood flow in a bleeding blood vessel and outputting a sensing signal. The warning indicator is in signal communication with the sensor and is configured for generating a message that corresponds to the sensing signal and indicates the smoothness of blood flow. In other words, the sensor fixed on the bandage can output a sensing signal corresponding to the smoothness of blood flow, and the warning indicator can automatically output a message indicating the smoothness of blood flow. This allows one who is undergoing a hemodialysis session to know the condition of the fistula directly from the message output by the warning indicator. When the fistula is subsequently under compression for hemostasis, there is also no need to listen to the sound of blood flow in the fistula with a stethoscope. The lack of an automatic pressure feedback and adjustment mechanism, however, still allows the entire tourniquet device to apply an excessively large pressure during use such that tissue hypoxia takes place due to insufficient blood supply to peripheral microcirculation. The tourniquet device, therefore, leaves something to be desired in use.

As another example of improved tourniquets, Taiwan Invention Patent No. I533835, entitled "Smart Proper Pressure Tourniquet" and published on May 21, 2016, discloses a smart proper pressure tourniquet that includes a strap, a controller provided on the outer surface of the strap, an air pocket provided inside the strap, and a pressure board provided on the inner surface of the strap. The controller is provided therein with a pressurizing unit, a pressure relief valve, a pressure sensing unit, and a control IC chip. The pressurizing unit, the pressure relief valve, and the pressure sensing unit are in communication with the air pocket separately. The control IC chip is separately and electrically connected to the pressurizing unit, the pressure relief valve, and the pressure sensing unit. The pressure sensing unit is configured for sensing the mean arterial pressure (MAP) of an area where hemostasis is to be achieved. The control IC chip, the pressurizing unit, and the pressure relief valve work together in order for the pressure board to apply a hemostatic pressure to the area where hemostasis is to be achieved. As the smart proper pressure tourniquet and its hemostatic method use only the pressure board to apply pressure to the area where hemostasis is to be achieved (i.e., a bleeding puncture), the bleeding stops slowly. For patients with coagulopathy, in particular, prolonged pressure application is required. While the I533835 invention allows the time needed for hemostasis to be set, the setting depends entirely on a medical professional's experience. If this medical professional makes the time setting without regard to the function of the patient's coagulation system, it is not unlikely that adequate hemostasis has yet to be achieved when the time is up and the smart proper pressure tourniquet, detached. Conversely, the time required for hemostasis cannot be set too long for a patient whose coagulation system is highly active due to medication; otherwise, fistula failure may result.

It is therefore crucial to develop an effective hemostatic method that can avoid overly high hemostatic pressure and reduce a patient's discomfort during the hemostatic process. In fact, using a hemostatic pressure lower than the systolic pressure helps protect a fistula from undue compression during the hemostatic process and can thereby extend the service life of the fistula effectively.

BRIEF SUMMARY OF THE INVENTION

In view of the fact that the conventional hemostatic methods based on single-point pressure application have the aforesaid drawbacks during use, the present invention provides a hemostatic method including the steps of: A) applying an at-puncture hemostatic pressure to a puncture in a blood vessel via a main geometric side, and applying at least one off-puncture hemostatic pressure to at least one position away from the puncture via at least one auxiliary geometric side, wherein the off-puncture hemostatic pressure acts on the blood vessel either directly or indirectly; and B) during the hemostatic process, obtaining an ongoing flow velocity of the blood in the blood vessel, and rendering the ongoing flow velocity lower than a normal flow velocity in the blood vessel by applying the at-puncture hemostatic pressure and the off-puncture hemostatic pressure simultaneously, wherein the at-puncture hemostatic pressure and the off-puncture hemostatic pressure are lower than a systolic pressure in the blood vessel.

Preferably, the step B includes rendering the ongoing flow velocity lower than 60% of the normal flow velocity.

Preferably, there is more than one auxiliary geometric side, the main geometric side has a main geometric center, each auxiliary geometric side has an auxiliary geometric center, and the auxiliary geometric centers are equidistant from the main geometric center.

Alternatively, there is more than one auxiliary geometric side, the main geometric side has a main geometric center, each auxiliary geometric side has an auxiliary geometric center, and the auxiliary geometric centers are not equidistant from the main geometric center.

Preferably, each auxiliary geometric center is 0.5 cm to 3.5 cm away from the main geometric center.

Preferably, the main geometric side has a main geometric side periphery, each auxiliary geometric side has an auxiliary geometric side periphery, and the shortest distance between the main geometric side periphery and the auxiliary geometric side peripheries is greater than 0 cm and smaller than 3.5 cm.

Preferably, the off-puncture hemostatic pressure is equal to the at-puncture hemostatic pressure.

Preferably, the step B includes obtaining a plurality of ongoing flow velocities at different times respectively and changing the at-puncture hemostatic pressure and/or the off-puncture hemostatic pressure during the hemostatic process according to each ongoing flow velocity obtained.

Preferably, the step B includes obtaining the ongoing flow velocity via an optical or ultrasonic measuring device.

Preferably, the at-puncture hemostatic pressure and the off-puncture hemostatic pressure are provided by operating a pressurizing device manually.

Alternatively, the at-puncture hemostatic pressure and the off-puncture hemostatic pressure are provided by controlling a pressurizing device through a computer program.

The hemostatic method further includes the step C, to be performed by a controller during the hemostatic process, of gathering one or a combination of the following pieces of information: the at-puncture hemostatic pressure, the off-puncture hemostatic pressure, the ongoing flow velocity, the systolic pressure, the duration of hemostatic operation, the working temperature of the main geometric side, and the working temperature of the auxiliary geometric side.

Preferably, the step C further includes outputting the gathered information via the controller.

Preferably, the step C further includes comparing the gathered information with a predetermined value and selectively outputting a notification signal according to the comparison result.

Based on the foregoing technical features, the present invention has the following advantages:

1. In contrast to the conventional single-point hemostatic methods, the hemostatic method of the present invention applies pressure to multiple points at the same time so that a relatively small hemostatic pressure suffices to achieve hemostasis. According to the present invention, the hemostatic pressure can be lower than the systolic pressure of the blood vessel of interest, thus greatly reducing the discomfort of the hemostatic process.

2. The method of the present invention can be used to stop a radial artery from bleeding after a PTCA operation has been performed therethrough, an AV fistula from bleeding after hemodialysis has been performed therethrough, an artery or vein in an extremity from bleeding after an arterial or venous catheter has been removed therefrom, and so on. With a main hemostatic element and at least one auxiliary hemostatic element pressed respectively against a puncture and a position adjacent to the puncture (i.e., with multipoint pressure application), hemostasis can be achieved with a relatively small hemostatic pressure to effectively protect a fistula from constriction or obstruction attributable to overcompression, reduce possible impact on and complication of the fistula, lower the frequency of fistula reconstruction, and thereby ensure the patient's safety.

BRIEF DESCRIPTION OF THE SEVERAL VIEWS OF THE DRAWINGS

FIG. 1 is a flowchart of the method of the present invention;

FIG. 10 shows curves for comparing the pressure values of single-point, two-point, and four-point pressure application and the resulting flow velocity reduction percentages;

FIG. 15 schematically shows how a single-point hemostatic element is pressed on an artificial fistula to simulate compression for hemostasis;

FIG. 16 schematically shows how a two-point hemostatic element is pressed on an artificial fistula to simulate compression for hemostasis.

DETAILED DESCRIPTION OF THE INVENTION

Figure 2:
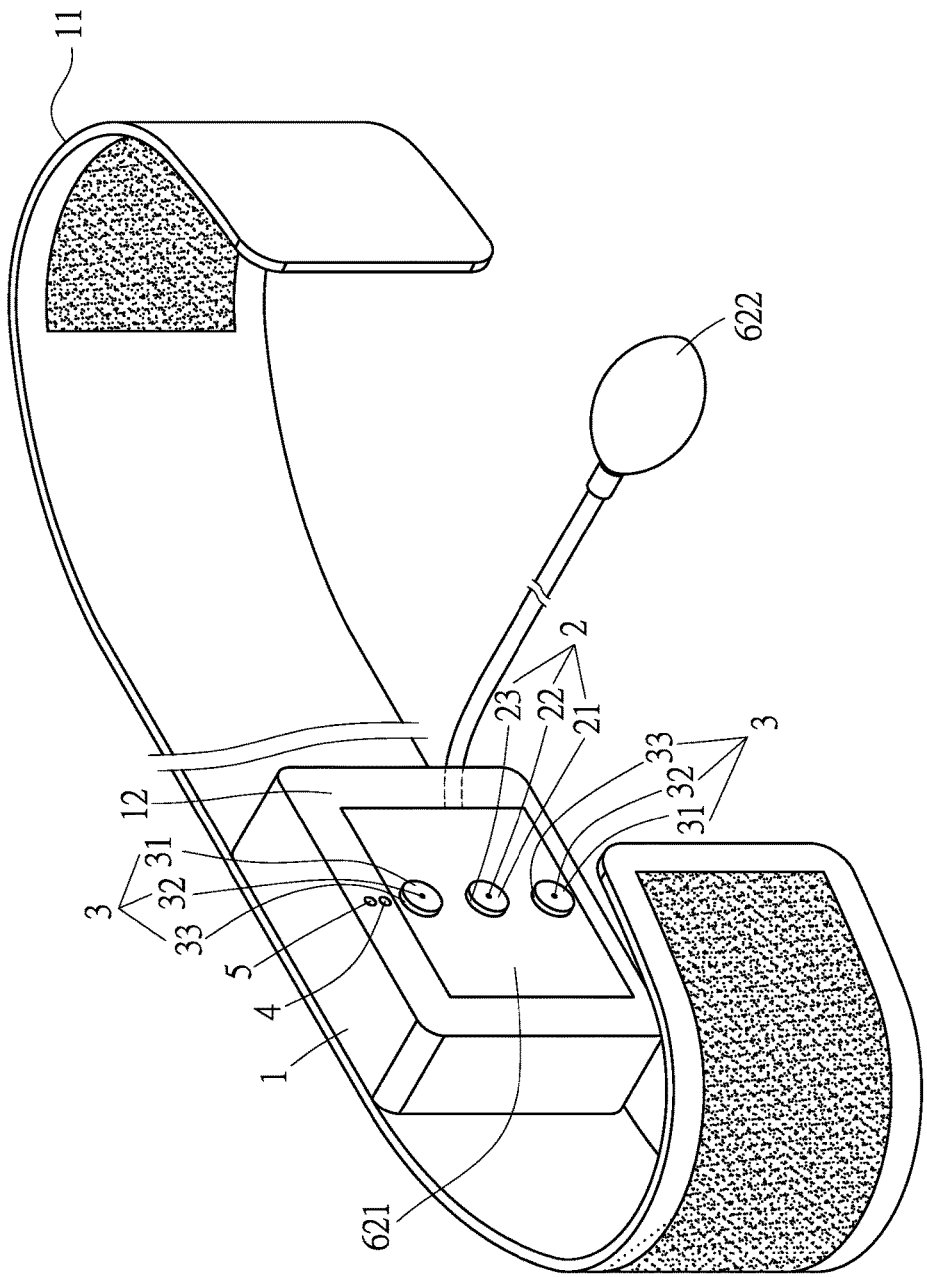
FIG. 2 is a perspective view of the hemostatic device of the present invention.

Referring to FIG. 1 and FIG. 2, the hemostatic method of the present invention can be carried out through a hemostatic device that includes a main body 1, a main hemostatic element 2, at least one auxiliary hemostatic element 3, a flow sensor 4, a pressure sensor 5, and a controller 6.

The main body 1 is provided with a strap 11 and a hemostatic side 12.

The main hemostatic element 2 is provided on the hemostatic side 12 and has a main geometric side 21. The main geometric side 21 has a main geometric center 22 and a main geometric side periphery 23.

The at least one auxiliary hemostatic element 3 is also provided on the hemostatic side 12. Each of the at least one auxiliary hemostatic element 3 has an auxiliary geometric side 31 with an auxiliary geometric center 32 and an auxiliary geometric side periphery 33.

Figure 3:
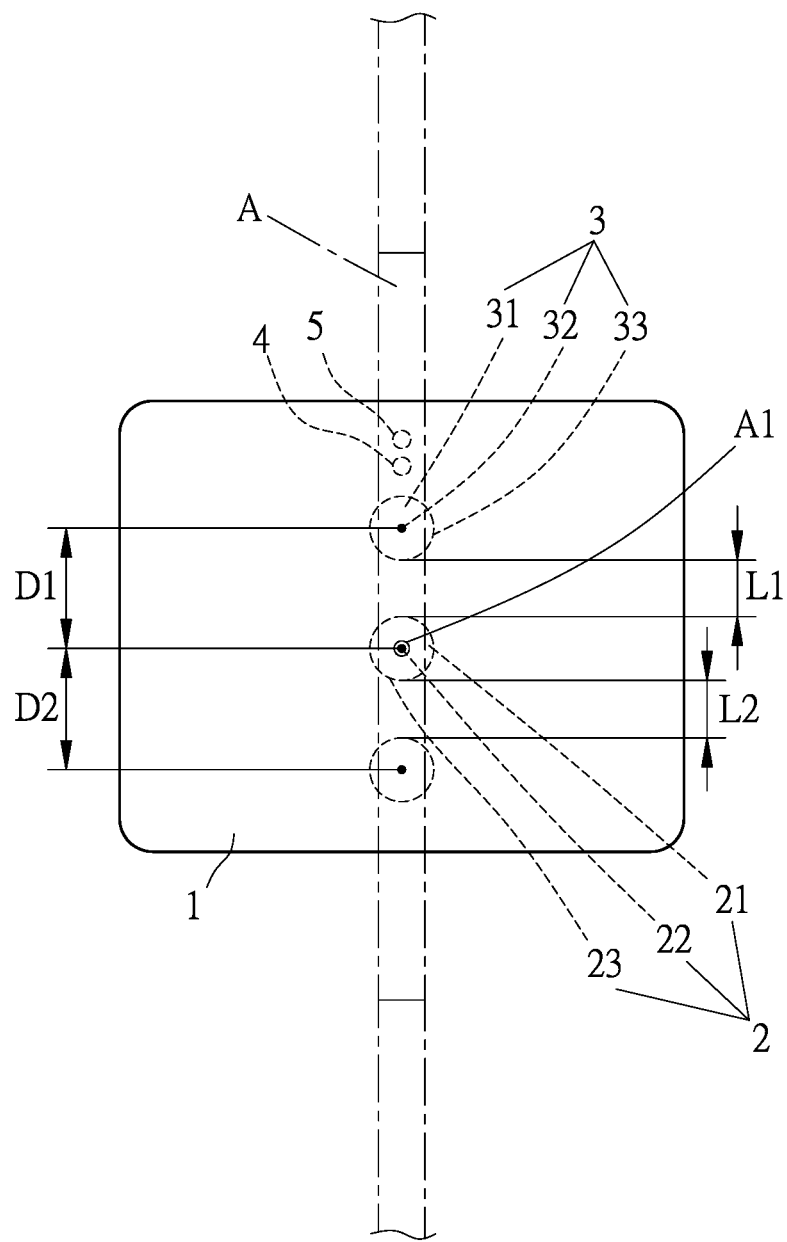
FIG. 3 shows that the main hemostatic element and two auxiliary hemostatic elements of the present invention are arranged along a predetermined line at equal spacing.
Figure 4:
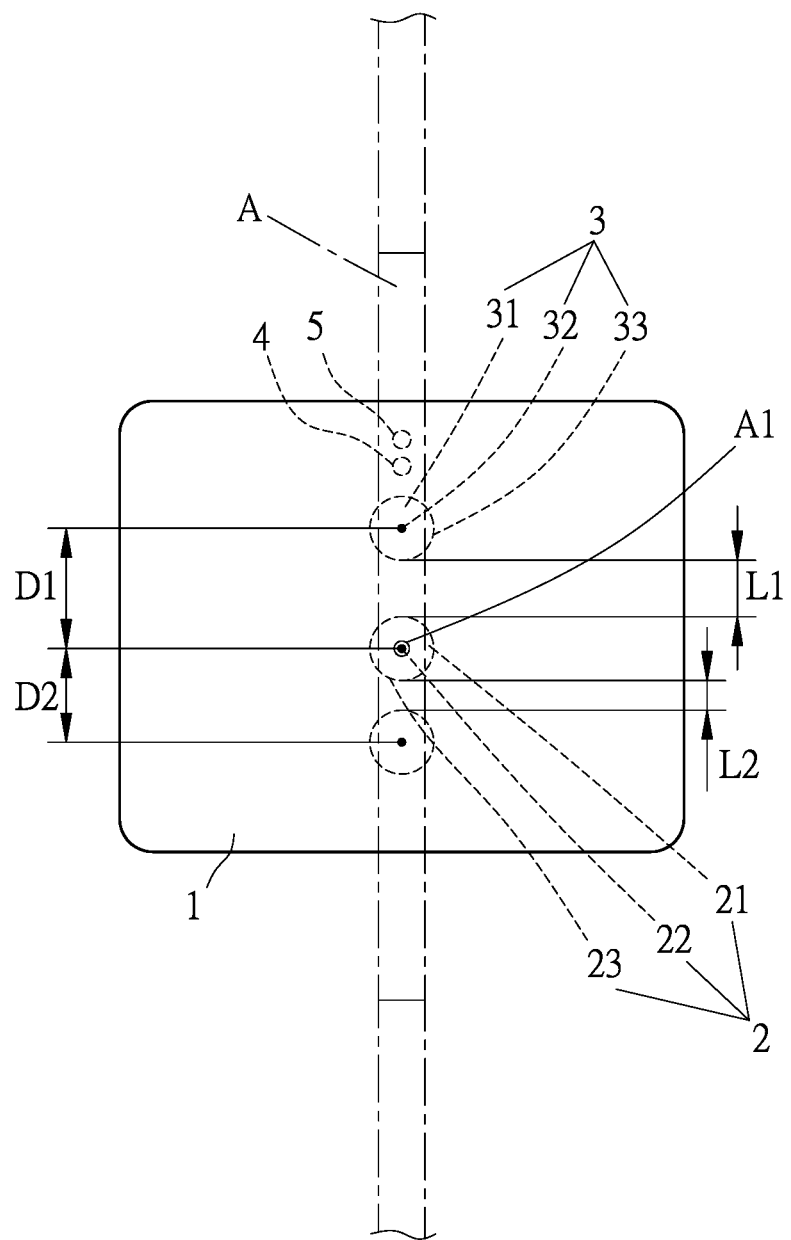
FIG. 4 shows that the main hemostatic element and two auxiliary hemostatic elements of the present invention are arranged along a predetermined line at unequal spacing.

In this embodiment, as shown in FIG. 3 and FIG. 4, there is one main hemostatic element 2 and two auxiliary hemostatic elements 3. The distance D1 between the main geometric center 22 and one of the auxiliary geometric centers 32 may be equal or unequal to the distance D2 between the main geometric center 22 and the other auxiliary geometric center 32. In this embodiment, the distances D1 and D2 between the main geometric center 22 and the auxiliary geometric centers 32 range from 0.5 cm to 3.5 cm. In addition, the shortest distance L1 (or L2) between the main geometric side periphery 23 and the auxiliary geometric side peripheries 33 is greater than 0 cm and smaller than 3.5 cm. If the auxiliary geometric centers 32 are too far away from the main geometric center 22, the auxiliary hemostatic elements 3 will be unable to produce the intended pressure application and hemostatic effect.

Figure 5:
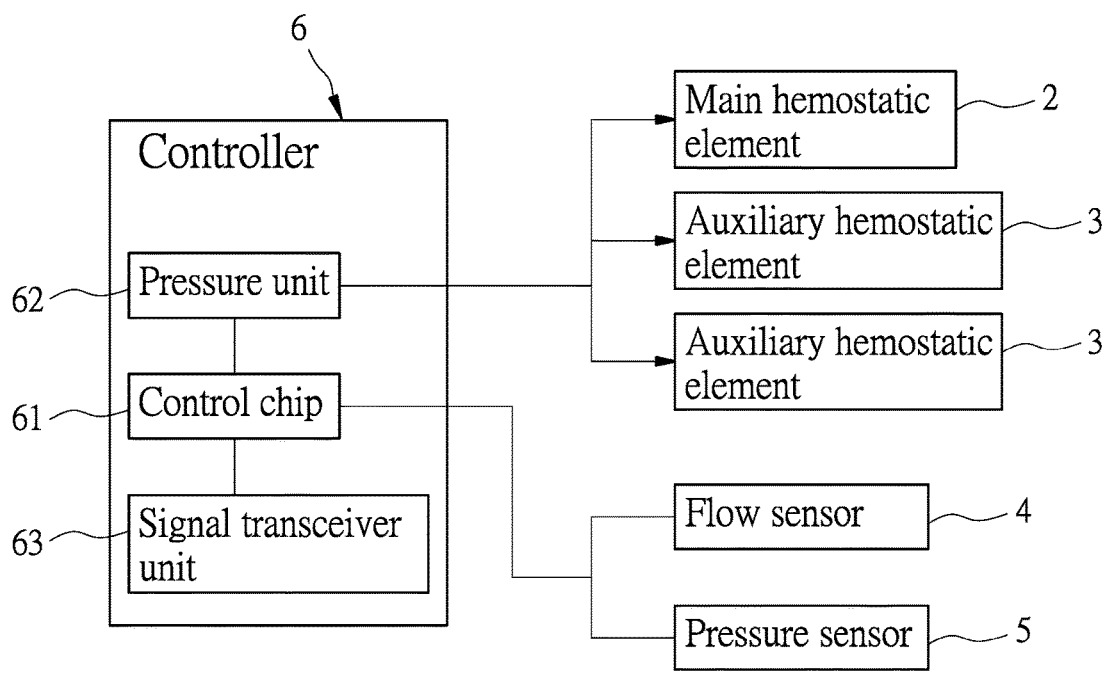
FIG. 5 is a block diagram showing the configuration of the controller of the present invention and the relationship between the controller and the components controlled thereby.
Figure 6:
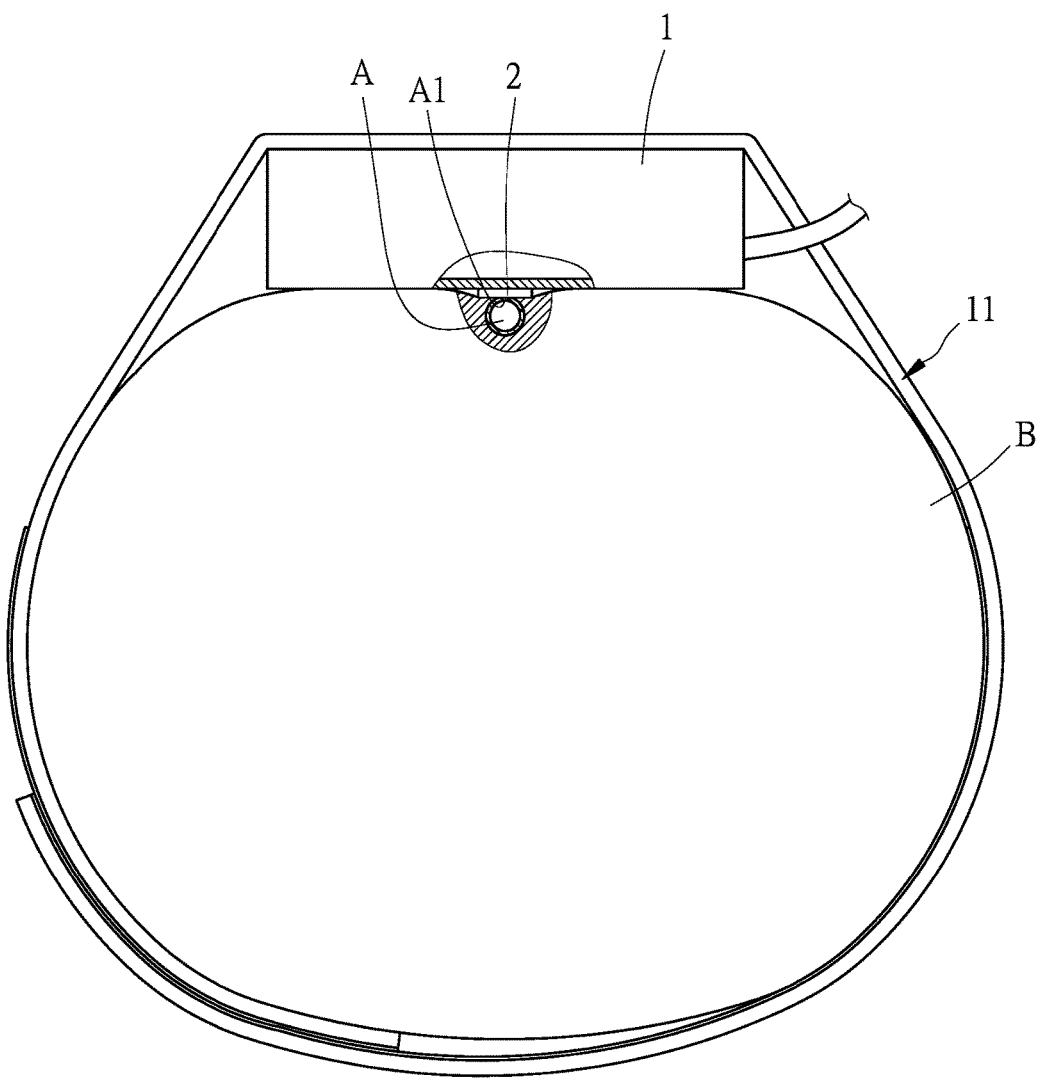
FIG. 6 shows the present invention being used for hemostasis.

Referring to FIG. 2, FIG. 3, and FIG. 5, the flow sensor 4 is provided on the hemostatic side 12 and is configured for detecting the normal flow velocity in a blood vessel A and the flow velocity in the blood vessel A during a hemostatic process. It is worth mentioning that the normal flow velocity varies from one person to another and in response to changes in physiological or psychological conditions. The flow sensor 4 may be an optical measuring device or an ultrasonic measuring device. In this embodiment, an optical measuring device is used by way of example.

The pressure sensor 5 is provided on the hemostatic side 12 and is configured for detecting the systolic pressure generated by the flood flow in the blood vessel A.

As shown in FIG. 2 and FIG. 5, the controller 6 is provided inside the main body 1. The controller 6 has a control chip 61 electrically connected to the flow sensor 4 and the pressure sensor 5 and configured for outputting a control signal, a pressure unit 62 electrically connected to the control chip 61, and a signal transceiver unit 63 electrically connected to the control chip 61 and configured for sending out the control signal output by the control chip 61. The pressure unit 62 may be configured for manual or automatic operation. When configured for manual operation, the pressure unit 62 may have an air pocket 621 configured to work in conjunction with the main hemostatic element 2 and the auxiliary hemostatic elements 3, an inflation blub 622 in communication with the air pocket 621, a relief valve (not shown) in communication with the air pocket 621 and electrically connected to the control chip 61, and a pressure gage (not shown) exposed to view and configured for displaying pressure values. The inflation bulb 622 is configured to be pressed manually in order to inflate the air pocket 621. Thus, by operating a pressurizing device (i.e., the air pocket 621) manually, the main hemostatic element 2 is enabled to apply an at-puncture hemostatic pressure (defined herein as a hemostatic pressure applied directly to a puncture), and each of the two auxiliary hemostatic elements 3, an off-puncture hemostatic pressure (defined herein as a hemostatic pressure applied to a position away from the puncture). The manual configuration is used in this embodiment by way of example.

When configured for automatic operation, the pressure unit 62 may have a pressurizing element (not shown) configured for working in conjunction with the main hemostatic element 2 and the auxiliary hemostatic elements 3, and a motor (not shown) electrically connected to the control chip 61 and configured for driving the pressurizing element in a timely manner under the control of the control chip 61. Thus, a computer program can be used to control a pressurizing device (i.e., the pressurizing element) and thereby enable the main hemostatic element 2 to apply an at-puncture hemostatic pressure and each of the two auxiliary hemostatic elements 3 to apply an off-puncture hemostatic pressure.

To implement the present invention, referring to FIG. 1 to FIG. 3 and FIG. 6, a preparation step can be performed in advance to obtain a systolic pressure of the blood vessel of interest and a normal flow velocity of the blood in the blood vessel. The hemostatic method in this embodiment of the present invention can be used, for example, to stop a radial artery from bleeding after a PTCA operation has been performed therethrough, an arteriovenous fistula (AV fistula) from bleeding after hemodialysis has been performed therethrough, and an artery or vein in an extremity from bleeding after an arterial or venous catheter has been removed therefrom. In this embodiment and by way of example, hemostasis is to be achieved for a puncture A1 in a blood vessel (i.e., fistula) A through which hemodialysis has been performed. After the dialysis treatment, a nurse removes the needle from the puncture A1, covers the puncture A1 with cotton at once, and performs single-point pressure application at the puncture A1. When bleeding is temporarily checked, the strap 11 is fastened around the patient's limb B such that the main hemostatic element 2 of the hemostatic device is pressed against the puncture A1 and the two auxiliary hemostatic elements 3, against areas adjacent to the puncture A1 respectively. The flow sensor 4 then detects variation in the normal flow velocity of the blood in the blood vessel A on a regular basis while the pressure sensor 5 detects the systolic pressure generated by the blood flow at the puncture A1. Aside from being measured in the hemostatic process, the systolic pressure may be a historical average derived for the patient from a database; both approaches work well in providing a reference systolic pressure value.

The hemostatic method in this embodiment of the present invention includes the following steps. In step A, an at-puncture hemostatic pressure is applied through a main geometric side to a puncture in a blood vessel, and at least one off-puncture hemostatic pressure is applied through at least one auxiliary geometric side to at least one position away from the puncture, wherein the off-puncture hemostatic pressure may act on the blood vessel directly or indirectly. More specifically, as shown in FIG. 2, FIG. 3, and FIG. 5, the inflation bulb 622 (i.e., a pressurizing device) is manually pressed to inflate the air pocket 621. Thus, the pressure unit 62 is driven to output a hemostatic pressure to the main hemostatic element 2 and each of the two auxiliary hemostatic elements 3, in order for the main hemostatic element 2 to apply an at-puncture hemostatic pressure to the puncture A1 via the main geometric side 21 while the auxiliary geometric side 31 of each auxiliary hemostatic element 3 is pressed against an area adjacent to the puncture A1 to provide compression for hemostasis. In this embodiment, the off-puncture hemostatic pressure is equal to the at-puncture hemostatic pressure.

In step B, which is performed during the hemostatic process, the flow velocity of the blood in the blood vessel is obtained, and this flow velocity (herein defined as the ongoing flow velocity) is reduced to lower than the normal flow velocity by simultaneous application of the at-puncture hemostatic pressure and the off-puncture hemostatic pressure, both lower than the systolic pressure. As the flow sensor 4 keeps detecting the flow velocity of the blood in the blood vessel A on a regular basis, a plurality of ongoing flow velocities are obtained, allowing the at-puncture hemostatic pressure at the puncture A1 and/or the off-puncture hemostatic pressure to be manually adjusted during the hemostatic process according to each ongoing flow velocity obtained. Please note that the at-puncture hemostatic pressure is directly applied through the main geometric side 21 to the puncture A1; that the off-puncture hemostatic pressure is applied through the auxiliary geometric sides 31, which are 0.5 cm to 3.5 cm away from the puncture A1; and that both the at-puncture hemostatic pressure and the off-puncture hemostatic pressure are lower than the systolic pressure. In this embodiment, the ongoing flow velocity is reduced to lower than 60% of the normal flow velocity, and bleeding is stopped when the hemostatic process ends.

Step C includes gathering information, outputting the information gathered, and providing a comparison result. During the hemostatic process, the control chip 61 of the controller 6 is used to gather one or a combination of the following pieces of information: the at-puncture hemostatic pressure, the off-puncture hemostatic pressure, the ongoing flow velocity, the systolic pressure, the duration of hemostatic operation, the working temperature of the main geometric side, and the working temperature of the auxiliary geometric side. Then, the controller 6 performs an information output sub-step, in which the information gathered is output through the signal transceiver unit 63. The controller 6 also compares the information gathered with a predetermined value and selectively outputs a notification signal according to the comparison result. The notification signal is displayed on the main body 1 or is output to a remote portable electronic device (e.g., a smartphone) for display.

Figure 7:
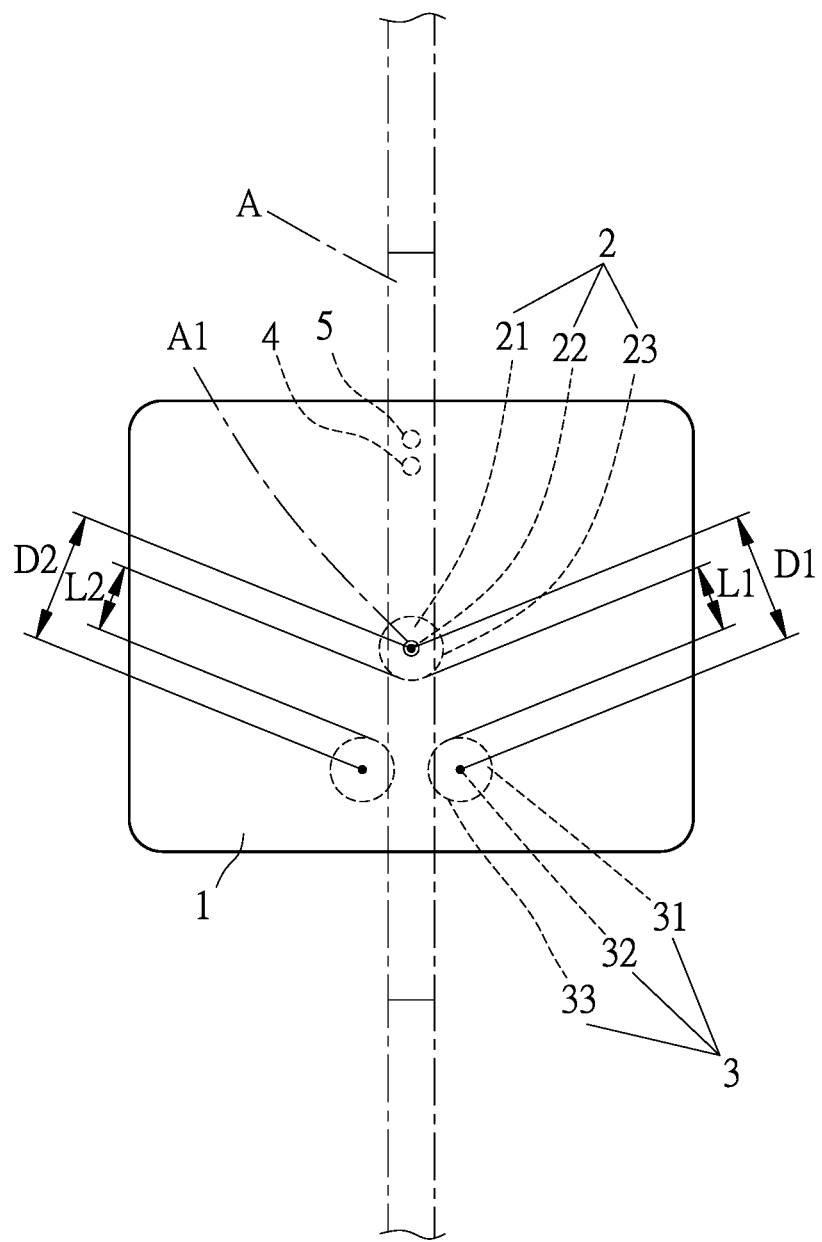
FIG. 7 shows that the main hemostatic element and two auxiliary hemostatic elements of the present invention are not arranged along a predetermined line, and that the auxiliary hemostatic elements are equidistant from the main hemostatic element.

Referring to FIG. 7, the main hemostatic element 2 and the auxiliary hemostatic elements 3 are not arranged along a predetermined line, and yet the distance D1 from one of the auxiliary geometric centers 32 to the main geometric center 22 is equal to the distance D2 from the other auxiliary geometric center 32 to the main geometric center 22. Furthermore, both auxiliary hemostatic elements 3 are adjacent to the main hemostatic element 2. In the embodiment shown in FIG. 7, the main hemostatic element 2 is pressed directly against the puncture A1 of the blood vessel A while the two auxiliary hemostatic elements 3 are pressed against areas beside the blood vessel A respectively. This arrangement is equally effective in compressing, and thereby stopping bleeding from, the blood vessel A.

Figure 8:
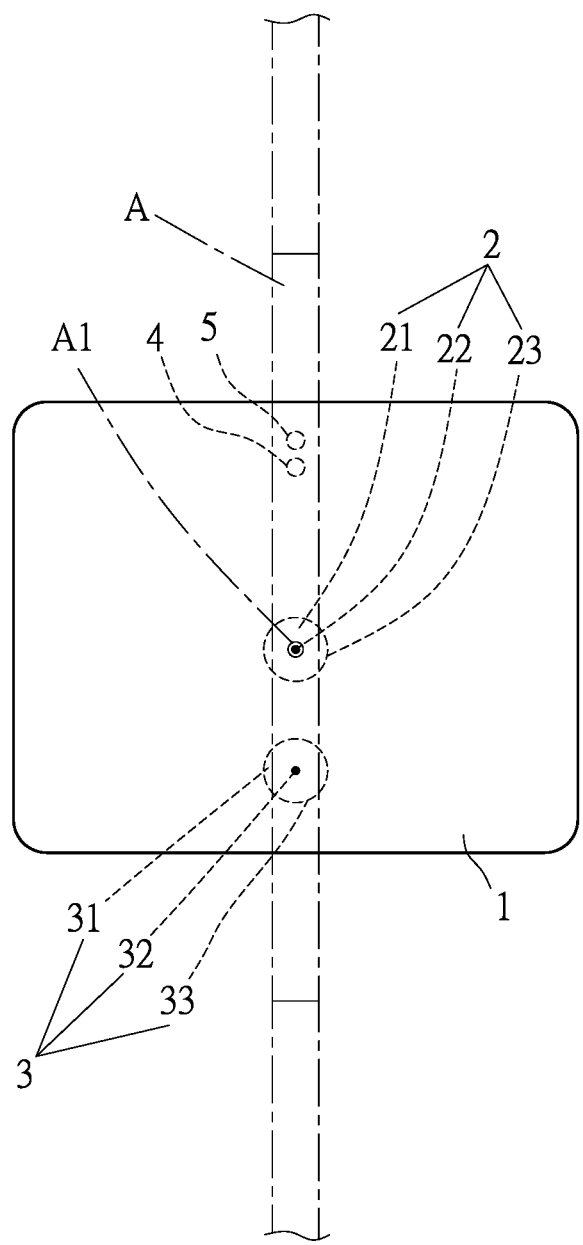
FIG. 8 shows that the main hemostatic element and an auxiliary hemostatic element of the present invention are arranged along a predetermined line.

In the embodiment shown in FIG. 8, there is only one auxiliary hemostatic element 3, and the main hemostatic element 2 and the auxiliary hemostatic element 3 are arranged along a predetermined line. This arrangement of the main hemostatic element 2 and the auxiliary hemostatic element 3 is equally effective in compressing, and thereby stopping bleeding from, the blood vessel A.

Figure 9:
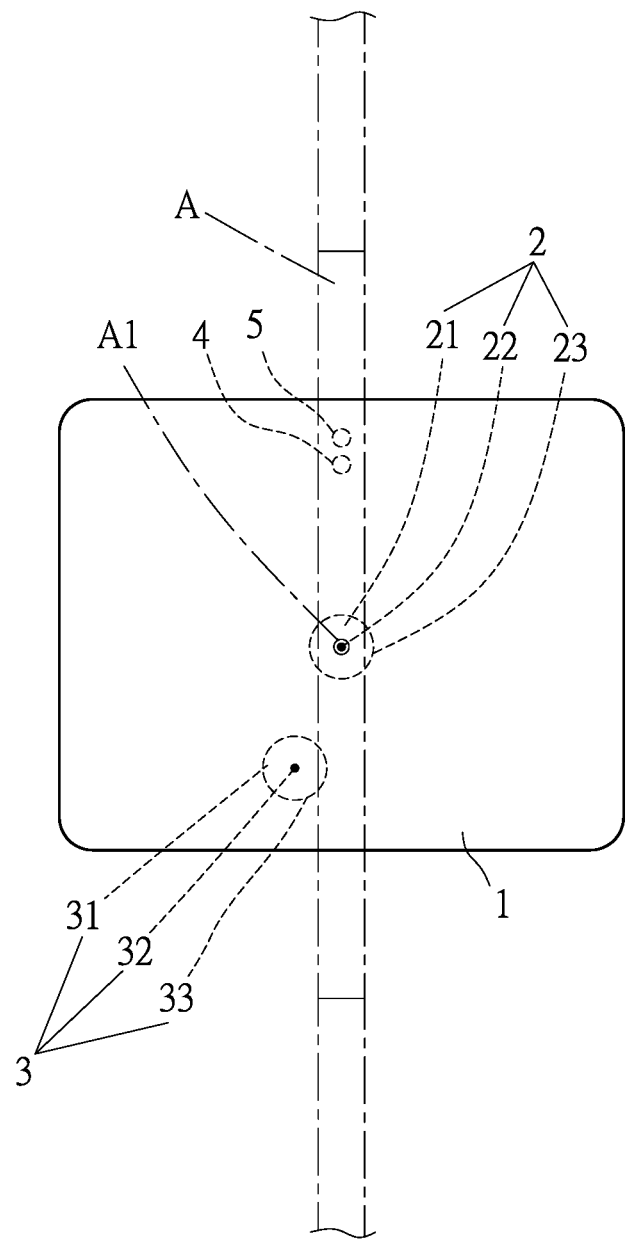
FIG. 9 shows that the main hemostatic element and an auxiliary hemostatic element of the present invention are not arranged along a predetermined line.

In the embodiment shown in FIG. 9, there is only one auxiliary hemostatic element 3, and the main hemostatic element 2 and the auxiliary hemostatic element 3 are not arranged along a predetermined line. This arrangement of the main hemostatic element 2 and the auxiliary hemostatic element 3 is still effective in compressing, and thereby stopping bleeding from, the blood vessel A.

In a simulated experiment environment, a flexible tube was used to simulate a blood vessel and was subjected to single-point, two-point, and four-point pressure application. The experiment results are shown in FIG. 10. Given the same pressure, a more significant reduction in flow velocity was achieved by two-point pressure application and four-point pressure application than by single-point pressure application. Taking the pressure of 120 mmHg for example, flow velocity dropped by 19.7% with single-point pressure application, 50.4% with two-point pressure application, and 81.6% with four-point pressure application. The hemostatic method of the present invention uses a multipoint pressure application design (e.g., the two-point or four-point pressure application design in the experiments), in which one main hemostatic element 2 is pressed against the puncture A1 while at least one auxiliary hemostatic element 3 is pressed against an area adjacent to the puncture A1 to overcome the drawback of the conventional single-point pressure application methods, namely the use of an overly high pressure (typically higher than 200 mmHg) that, although essential to hemostasis, may lead to blood vessel injury or other injuries associated with hypoxia of peripheral tissues. Generally, effective hemostasis is achieved when the flow velocity of blood is lowered by 60%, at which time blood can still flow smoothly in the blood vessel. This criterion may nevertheless vary with a patient's body constitution and the condition of the puncture wound. Moreover, when the flow velocity is reduced by 60%, referring to FIG. 10, the pressure required of two-point pressure application is about 140 mmHg, and that required of four-point pressure application is only about 100 mmHg. This indicates that, when multipoint (e.g., two-point or four-point) pressure application is used in the hemostatic process, effective hemostasis can be achieved without resorting to an excessively large pressure (over 200 mmHg).

The hemostatic method disclosed herein has wide application. For instance, it can be used to stop a radial artery from bleeding after a PTCA operation has been performed therethrough, an AV fistula from bleeding after hemodialysis has been performed therethrough, and an artery or vein in an extremity from bleeding after an arterial or venous catheter has been removed therefrom. The method features easy operation, is user-friendly, and can effectively protect a fistula from over-compression during the hemostatic process, thereby reducing possible impact on and complication of the fistula, lowering the frequency of fistula reconstruction, and consequently ensuring the patient's safety. The hemostatic device disclosed herein is capable of pressure measurement and real-time feedback of the pressure applied, allowing the pressure value to be displayed by the hemostatic device or another portable electronic device (e.g., a smartphone). This technical feature allows a patient to put on the hemostatic device by themselves according to the pressure preset by a medical professional, and to know when hemostasis is achieved by watching a display screen on the hemostatic device. The hemostatic device may also provide physiological parameters (e.g., blood flow velocity, blood vessel pulse rate, or oxygen concentration in the blood) measured from the blood vessel in order for the patient to know the current health condition of the blood vessel and of their body.

Besides, referring back to FIG. 3 and FIG. 5, the controller 6 of the hemostatic device may have a timing unit (not shown) electrically connected to the control chip 61 and configured for timing the hemostatic process. When the preset duration of a hemostatic process has elapsed, the control chip 61 drives the pressure unit 62 to stop pressure application such that the main hemostatic element 2 and the auxiliary hemostatic elements 3 are released from the puncture A1 and the neighboring pressed areas to minimize injury caused by compression of the blood vessel A. The controller 6 may also connect to a cloud database through the Internet in order to acquire recommended medical care data that are uploaded remotely. For example, a remote medical professional can provide a recommended hemostatic process duration according to a patient's body condition or medication. If the patient takes an anticoagulant, for example, a two-hour extension of the hemostatic process would be advised.

To verify whether the present invention can be put to practice and achieve hemostasis without using an excessively large hemostatic pressure, the following simulation experiments were performed.

Figure 11:
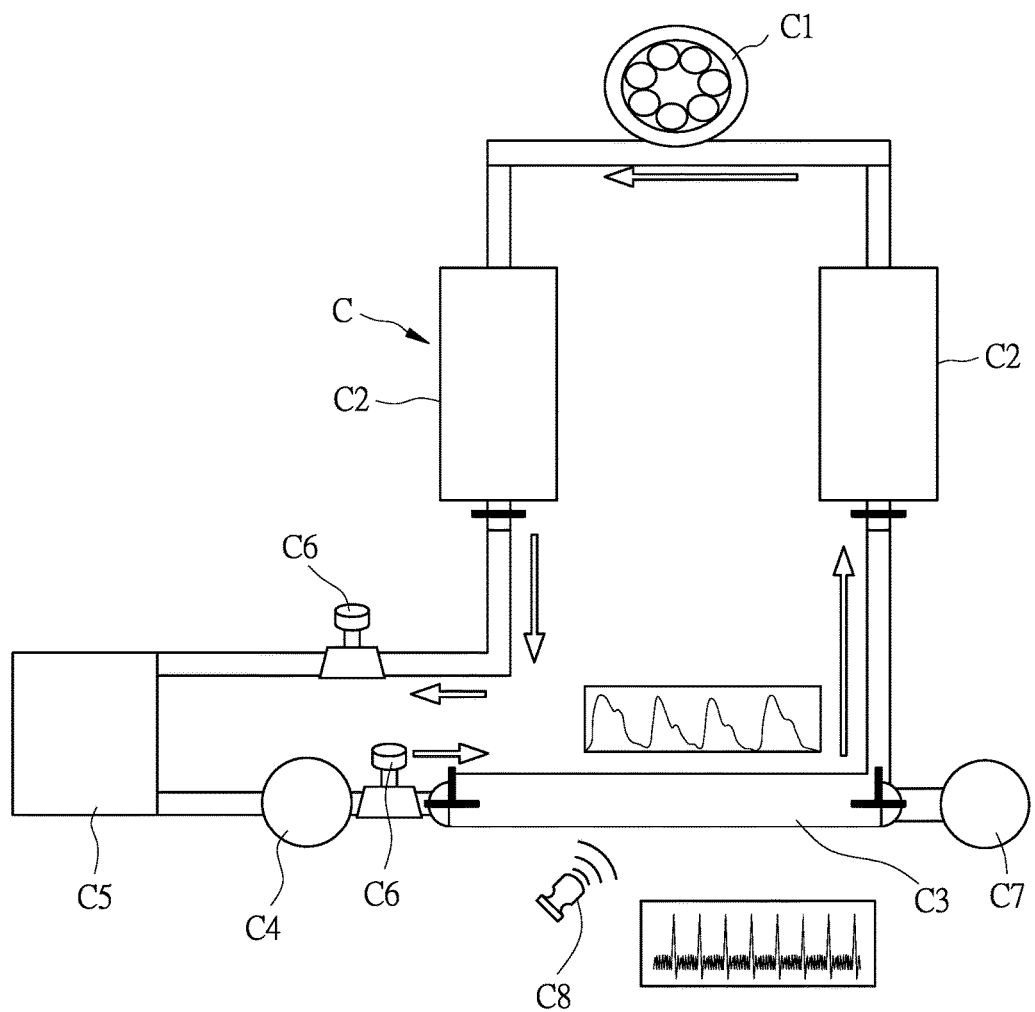
FIG. 11 schematically shows the simulation system of the present invention for performing pressure application experiments to achieve hemostasis.

To begin with, referring to FIG. 11, a closed simulation system C was constructed, in which a pulse motor C1 was provided to simulate the pumping function of a heart and two water pipes C2, to simulate an artery and a vein of the human body respectively. The two water pipes C2 were connected by a flexible artificial fistula C3 in simulation of an AV fistula. The front end of the artificial fistula C3 was further connected with a motor C4 and a water tank C5 such that a loop was formed. A blood-simulating liquid was then introduced into the system C, wherein the liquid was prepared by adding corn starch into artificial blood or normal saline for higher viscosity. In addition, a check valve C6 was installed downstream the motor C4, and another check valve C6, upstream the water tank C5, to facilitate water refill and pressure adjustment in the simulation system C. Pressure in the artificial fistula C3 was measured with a pressure gage C7. The flow velocity of the liquid in the artificial fistula C3 was detected with Doppler ultrasound C8.

Figure 12:
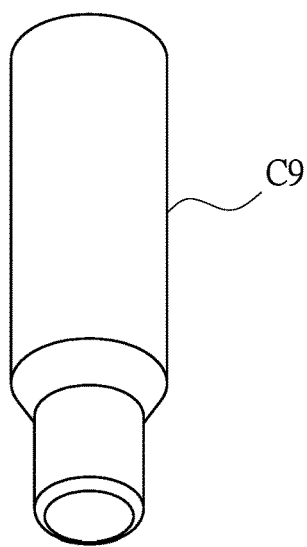
FIG. 12 is a perspective view of the single-point hemostatic element used in the experiments of the present invention.
Figure 13:
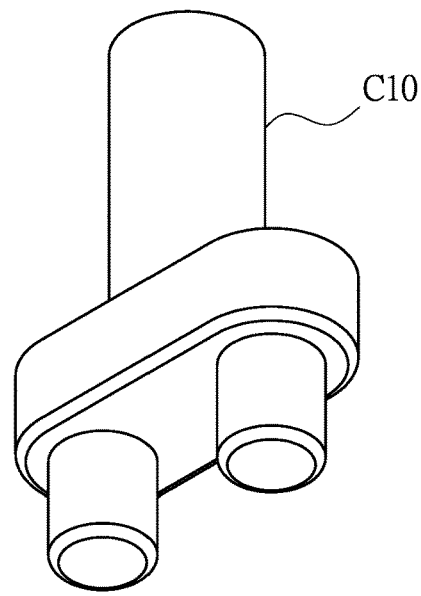
FIG. 13 is a perspective view of the two-point hemostatic element used in the experiments of the present invention.
Figure 14:
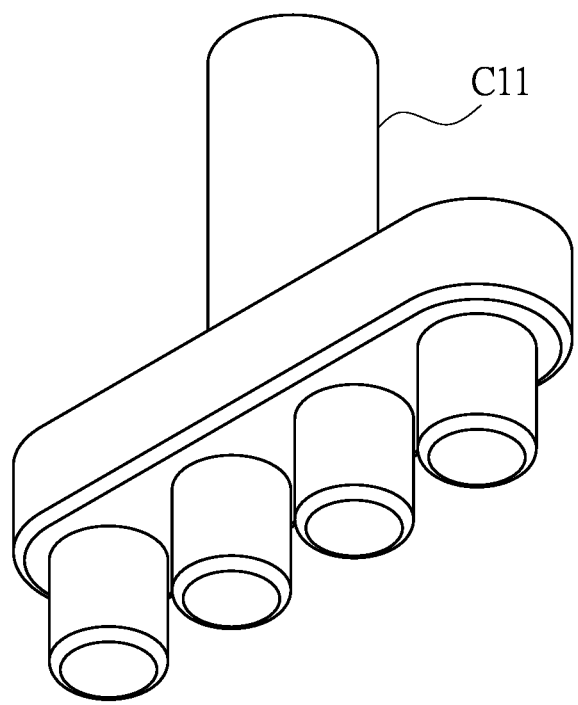
FIG. 14 is a perspective view of the four-equally-spaced-point hemostatic element used in the experiments of the present invention.
Figure 17:
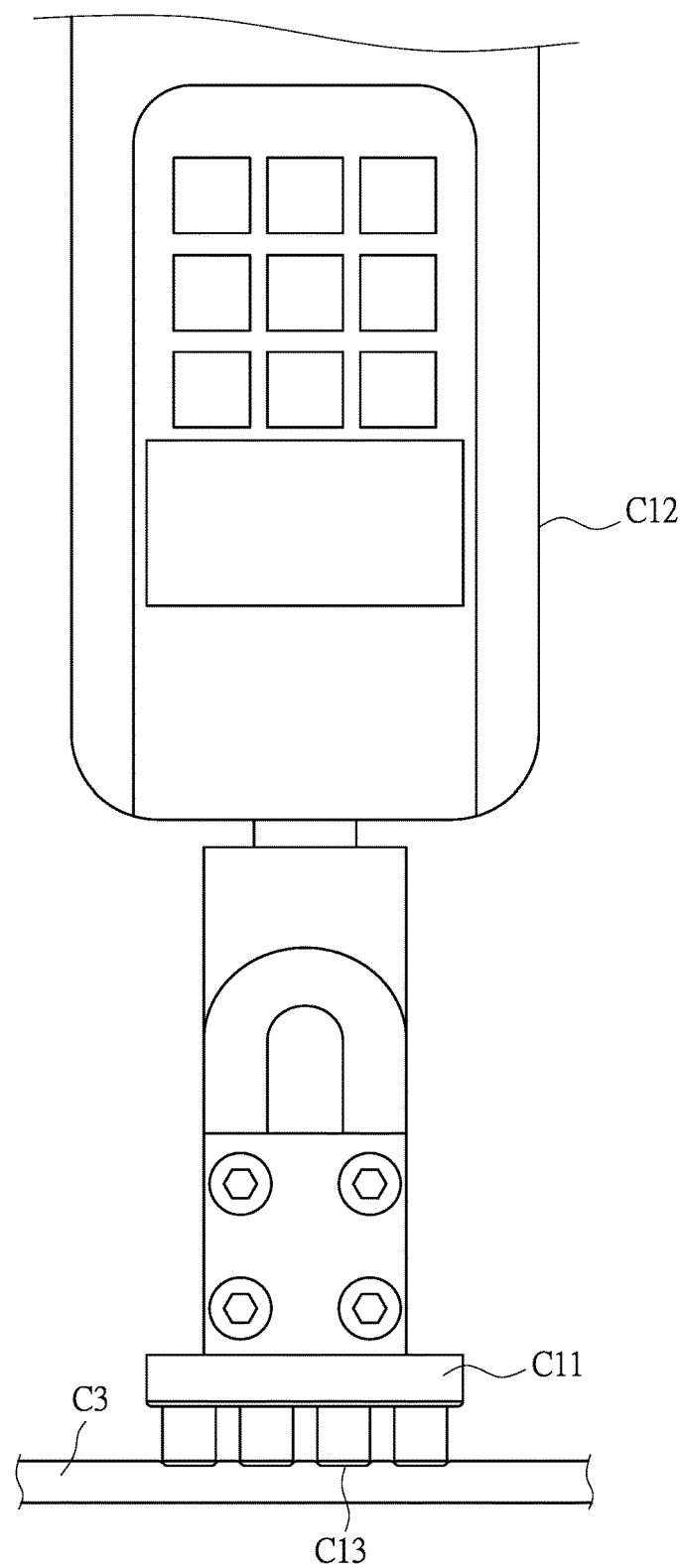
FIG. 17 schematically shows how a four-equally-spaced-point hemostatic element is pressed on an artificial fistula to simulate compression for hemostasis.

Referring to FIG. 12 to FIG. 14, a mold was provided with a single block to simulate a single-point hemostatic element C9, a mold was provided with two blocks to simulate a two-point hemostatic element C10, and a mold was provided with four equally spaced blocks to simulate a four-equally-spaced-point hemostatic element C11. Then, referring to FIG. 15 to FIG. 17, a pressure gage C12 was connected to each of the single-point hemostatic element C9, the two-point hemostatic element C10, and the four-equally-spaced-point hemostatic element C11 in order to simulate single-point, two-point, and four-equally-spaced-point pressure application to a simulated puncture C13 in the artificial fistula C3 respectively. The simulation results were plotted in FIG. 10, which shows curves representing the relationships between the pressure generated by single-point, two-point, and four-point pressure application and the resulting flow velocity reduction percentages.

The embodiments described above are only some preferred ones of the present invention and are not intended to be restrictive of the scope of the invention. All simple equivalent changes and substitutions made according to the disclosure of this specification and the appended claims are encompassed by the present invention.

What is claimed is:

1. A hemostatic method, comprising:
   A) providing a main hemostatic element having a main geometric side and at least one auxiliary hemostatic element having an auxiliary geometric side;
   B) performing a hemostatic process including (1) applying an at-puncture hemostatic pressure to a puncture in a blood vessel via the main geometric side of the main hemostatic element, and (2) applying at least one off-puncture hemostatic pressure to at least one position away from the puncture via the at least one auxiliary geometric side of the at least one auxiliary hemostatic element, wherein the at least one off-puncture hemostatic pressure acts on the blood vessel directly or indirectly; and
   C) obtaining an initial flow velocity in the blood vessel prior to performing the hemostatic process, obtaining an ongoing flow velocity of blood in the blood vessel during the hemostatic process, and rendering the ongoing flow velocity lower than the initial flow velocity in the blood vessel by applying the at-puncture hemostatic pressure and the at least one off-puncture hemostatic pressure simultaneously, wherein the at-puncture hemostatic pressure and the at least one off-puncture hemostatic pressure are lower than a systolic pressure in the blood vessel.

2. The hemostatic method of claim 1, wherein the step C includes rendering the ongoing flow velocity lower than 60% of the initial flow velocity.

3. The hemostatic method of claim 1, wherein said at least one auxiliary hemostatic element includes a plurality of auxiliary hemostatic elements each having a respective auxiliary geometric side, the main geometric side has a main geometric center, each said auxiliary geometric side has an auxiliary geometric center, and the auxiliary geometric centers are equidistantly spaced from the main geometric center.

4. The hemostatic method of claim 3, wherein each said auxiliary geometric center is 0.5 cm to 3.5 cm away from the main geometric center.

5. The hemostatic method of claim 3, wherein the main geometric side has a main geometric side periphery, each said auxiliary geometric side has an auxiliary geometric side periphery, and a shortest distance between the main geometric side periphery and the auxiliary geometric side peripheries is greater than 0 cm and smaller than 3.5 cm.

6. The hemostatic method of claim 1, wherein said at least one auxiliary hemostatic element includes a plurality of auxiliary hemostatic elements each having a respective auxiliary geometric side, the main geometric side has a main geometric center, each said auxiliary geometric side has an auxiliary geometric center, and the auxiliary geometric centers are non-equidistantly spaced from the main geometric center.

7. The hemostatic method of claim 6, wherein each said auxiliary geometric center is 0.5 cm to 3.5 cm away from the main geometric center.

8. The hemostatic method of claim 6, wherein the main geometric side has a main geometric side periphery, each said auxiliary geometric side has an auxiliary geometric side periphery, and a shortest distance between the main geometric side periphery and the auxiliary geometric side peripheries is greater than 0 cm and smaller than 3.5 cm.

9. The hemostatic method of claim 1, wherein the at least one off-puncture hemostatic pressure is equal to the at-puncture hemostatic pressure.

10. The hemostatic method of claim 1, wherein the step C includes obtaining a plurality of said ongoing flow velocities at different times respectively and changing the at-puncture hemostatic pressure and/or the at least one off-puncture hemostatic pressure during the hemostatic process according to each said ongoing flow velocity obtained.

11. The hemostatic method of claim 1, wherein the step C includes obtaining the ongoing flow velocity via an optical or ultrasonic measuring device.

12. The hemostatic method of claim 1, wherein the at-puncture hemostatic pressure and the at least one off-puncture hemostatic pressure are provided by operating a pressurizing device manually.

13. The hemostatic method of claim 1, wherein the at-puncture hemostatic pressure and the at least one off-puncture hemostatic pressure are provided by controlling a pressurizing device through a computer program.

14. The hemostatic method of claim 1, further comprising using a controller during the hemostatic process to gather one or more pieces of information selected from the group consisting of: the at-puncture hemostatic pressure, the at least one off-puncture hemostatic pressure, the ongoing flow velocity, the systolic pressure, a duration of hemostatic operation, a working temperature of the main geometric side, and a working temperature of the auxiliary geometric side.

15. The hemostatic method of claim 14, wherein the step of using a controller during the hemostatic process to gather one or more pieces of information further includes outputting the gathered information via the controller.

16. The hemostatic method of claim 15, wherein the step of using a controller during the hemostatic process to gather one or more pieces of information further includes comparing the gathered information with a predetermined value and selectively outputting a notification signal according to a comparison result.

* * * * *